(12) United States Patent
Chambers et al.

(10) Patent No.: US 7,482,457 B2
(45) Date of Patent: Jan. 27, 2009

(54) SUBSTITUTED QUINOLINE-4-CARBOXYLIC HYDRAZIDES AS NK-2/NK-3 RECEPTOR LIGANDS

(75) Inventors: Mark Stuart Chambers, Puckeridge (GB); Philip Jones, Pomezia (IT); Angus Murray MacLeod, Bishops Stortford (GB)

(73) Assignee: Merck Sharp & Dohme, Hoddesdon, Hertfordshire ( * ) Notice: Subject to any disclaimer, the term of this patent is extended or adjusted under 35 U.S.C. 154(b) by 609 days.

(21) Appl. No.: 10/544,440

(22) PCT Filed: Feb. 3, 2004

(86) PCT No.: PCT/GB2004/000415

§ 371 (c)(1),
(2), (4) Date: Aug. 4, 2005

(87) PCT Pub. No.: WO2004/072045

PCT Pub. Date: Aug. 26, 2004

(65) Prior Publication Data

US 2006/0089348 A1    Apr. 27, 2006

(30) Foreign Application Priority Data

Feb. 11, 2003    (GB) .................... 0303086.3

(51) Int. Cl.
*C07D 215/38* (2006.01)
(52) U.S. Cl. .................... 546/168; 546/153; 546/156
(58) Field of Classification Search ................. 546/153, 546/156, 168; 514/312, 313, 314
See application file for complete search history.

(56) References Cited

FOREIGN PATENT DOCUMENTS

| WO | WO 96/02509 | 2/1996 |
|---|---|---|
| WO | WO 97/21680 | 6/1997 |
| WO | WO 00/31037 | 6/2000 |
| WO | WO 02/083645 | 10/2002 |

OTHER PUBLICATIONS

Bavin, CA 47:10106, abstract only of J of pHarm and Pharmacology, vol. 4, pp. 844-854, 1952.*
Chemical Abstracts, vol. 103, No. 7, Aug. 19, 1985, p. 564; col. 2.

* cited by examiner

*Primary Examiner*—D. Margaret Seaman
(74) *Attorney, Agent, or Firm*—J. Eric Thies; William Krovatin

(57) ABSTRACT

The present invention discloses a compound of formula (I): wherein: $R^1$ is an aryl or heteroaryl ring; $R^2$ is hydroxy, $C_{1-6}$ alkoxy, $C_{1-6}$ alkyl, amino, NR'R" or $C_{1-6}$ alkyl-NR'R" where R' and R" are independently chosen from hydrogen and $C_{1-4}$ alkyl and where R' and R", together with the nitrogen atom to which they are attached, form a saturated nitrogen-containing 3-7 membered heterocycle optionally containing a further nitrogen atom and optionally substituted by NR'R" as defined above or $R^2$ is $C_{1-6}$ alkoxy substituted by NR'R" as defined above; $R^3$ is hydrogen or $C_{1-6}$ alkyl; $R^4$ is hydrogen, $C_{1-8}$ alkyl, $C_{2-8}$ alkenyl, $C_{2-8}$ alkynyl, $C_{3-8}$ cycloalkyl, aryl or aryl $C_{1-6}$ alkyl; $R^5$ is hydrogen, $C_{1-8}$ alkyl, $C_{2-8}$ alkenyl, $C_{2-8}$ alkynyl, $C_{3-8}$ cycloalkyl, aryl, aryl $C_{1-6}$ alkyl or $C_{1-6}$ alkoxycarbonyl; or $R^4$ and $R^5$, together with the nitrogen atom to which they are attached, form a $C_3$-$C_{10}$ mono- or bicyclic saturated ring; X and Y are independently chosen from hydrogen, hydroxy, nitro, amino, cyano, $CF_3$, halogen and $C_{1-4}$ alkyl; or a pharmaceutically acceptable salt thereof; as NK-2/NK-3 ligands for treating schizophrenia, COPD, asthma or irritable bowel syndrome.

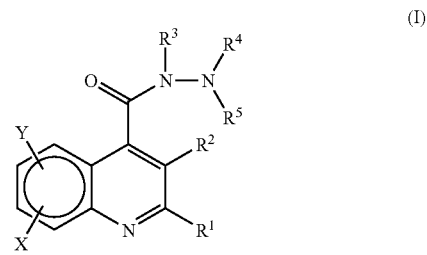

12 Claims, No Drawings

SUBSTITUTED QUINOLINE-4-CARBOXYLIC HYDRAZIDES AS NK-2/NK-3 RECEPTOR LIGANDS

CROSS REFERENCE TO RELATED APPLICATIONS

This application is a U.S. National Phase application under 35 U.S.C. § 371 of PCT Application No. PCT/GB2004/000415, filed Feb. 3, 2004, which claims priority under 35 U.S.C. § 119 from GB Application No. 0303086.3, filed Feb. 11, 2003.

The present invention relates to substituted quinoline-4-carboxylic acid hydrazides defined herein, pharmaceutical composition comprising them and their use in treating diseases mediated by neurokinin-2 and/or neurokinin-3 (NK-3) receptors. These compounds can thus be used in methods of treatment to suppress and treat such disorders.

Background information on NK-3 receptor antagonists can be found in literature reviews such as Giardina and Raveglia, Exp. Opin. Ther. Patents (1997) 7(4): 307-323 and Giardina et al, Exp. Opin. Ther. Patents (2000) 10(6): 939-960. These references also contain pertinent information on preclinical validation of therapies that can be treated with NK-3 antagonists.

Representative examples of compounds prepared in the art as NK-3 antagonists are to be found in WO-A-9719926 (SmithKline Beecham S.p.a.) and U.S. Pat. No. 5,741,910 (Sanofi).

The present invention thus provides the use of a compound of Formula (I):

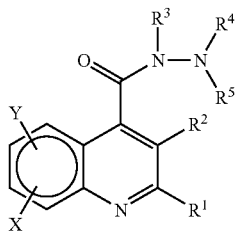

wherein:

$R^1$ is an aryl or heteroaryl ring, wherein aryl is phenyl or naphthyl and heteroaryl is a 5-membered unsaturated ring containing 1, 2, 3 or 4 nitrogen atoms and/or, an oxygen or sulphur atom provided no more than two nitrogen atoms are present, or a 6-membered unsaturated ring containing 1, 2 or 3 nitrogen atoms, said ring being optionally substituted by one, two or three groups independently chosen from hydroxy, halogen, nitro, cyano, amino, $CF_3$, $C_{1-4}$ alkyl, $C_{2-4}$ alkenyl and $C_{2-4}$ alkynyl;

$R^2$ is hydroxy, $C_{1-6}$ alkoxy, $C_{1-6}$ alkyl, amino, NR'R" or $C_{1-6}$ alkyl-NR'R" where R' and R" are independently chosen from hydrogen and $C_{1-4}$ alkyl and where R' and R", together with the nitrogen atom to which they are attached, form a saturated nitrogen-containing 3-7 membered heterocycle optionally containing a further nitrogen atom and optionally substituted by NR'R" as defined above or $R^2$ is $C_{1-6}$ alkoxy substituted by NR'R" as defined above;

$R^3$ is hydrogen or $C_{1-6}$ alkyl;

$R^4$ is hydrogen, $C_{1-8}$ alkyl, $C_{2-8}$ alkenyl, $C_{2-8}$ alkynyl, $C_{3-8}$ cycloalkyl, aryl or aryl $C_{1-6}$ alkyl;

$R^5$ is hydrogen, $C_{1-8}$ alkyl, $C_{2-8}$ alkenyl, $C_{2-8}$ alkynyl, $C_{3-8}$ cycloalkyl, aryl, aryl $C_{1-6}$ alkyl or $C_{1-6}$ alkoxycarbonyl;

or $R^4$ and $R^5$, together with the nitrogen atom to which they are attached, form a $C_3$-$C_{10}$ mono- or bicyclic saturated ring;

X and Y are independently chosen from hydrogen, hydroxy, nitro, amino, cyano, $CF_3$, halogen and $C_{1-4}$ alkyl;

or a pharmaceutically acceptable salt thereof.

$R^1$ is preferably unsubstituted or monosubstituted by hydroxy, halogen, nitro, cyano, amino, $CF_3$ or $CH_3$. $R^1$ is generally an aryl group, such as phenyl.

$R^2$ is preferably hydroxy, $C_{1-4}$ alkoxy, $C_{1-4}$ alkyl or $C_{1-4}$ alkyl substituted by NR'R". $R^2$ is especially methoxy, methyl or 4-N'-(1-methylethyl)piperazinyl-1-N-methylene.

R' and R" are preferably independently chosen from hydrogen, methyl, ethyl and propyl, or, R' and R", together with the nitrogen atom to which they are attached, form a piperidine or piperazine ring optionally substituted by $C_{1-4}$ alkyl. R' and R" preferably from a piperidine or piperazine ring together with the nitrogen atom to which they are attached which ring is optionally substituted by $C_{1-4}$ alkyl. Most preferably R' and R", together with the nitrogen atom to which they are attached, form an optionally substituted piperazine ring. The optional substituent is preferably propyl, particularly isopropyl.

$R^4$ is preferably $C_{1-8}$ alkyl, $C_{3-8}$ cycloalkyl, aryl or aryl $C_{1-6}$ alkyl. More preferably $R^4$ is $C_{1-6}$ alkyl, $C_{4-7}$ cycloalkyl or phenyl $C_{1-4}$ alkyl. Most preferably $R^4$ is phenyl, 1-phenylpropyl, isopropyl, cyclohexyl, cyclopentyl or benzyl.

$R^5$ is preferably hydrogen, $C_{1-6}$ alkyl, aryl or $C_{1-4}$ alkoxycarbonyl. More preferably $R^5$ is hydrogen, $C_{1-4}$ alkyl, phenyl or $C_{1-2}$ alkoxycarbonyl. Most preferably $R^5$ is hydrogen, methoxycarbonyl, ethyl, methyl or phenyl.

When $R^4$ and $R^5$ form a mono- or bicyclic ring together with the nitrogen atom to which they are attached, it preferably contains from 5 to 8 carbon atoms, such as azepanyl or hexahydrocyclopenta[c]pyrrol-2(1H)-yl.

X and Y are preferably hydrogen or methyl, most preferably hydrogen.

Compounds in which NR'R" forms a 3-7 membered heterocycle, and prefered definitions thereof, are particularly useful as NK-2 inhibitors.

The independent syntheses of any optical isomers or their chromatographic separations may be achieved as known in the art. Their absolute stereochemistry may be determined by the x-ray crystallography of crystalline products or crystalline intermediates which are derivatized, if necessary, with a reagent containing an asymmetric center of known absolute configuration.

As used herein, the term "$C_{1-8}$ alkyl" means linear or branched chain alkyl groups having from 1 to 8 carbon atoms and includes all of the octyl, heptyl, hexyl and pentyl alkyl isomers as well as n-, iso-, sec- and t-butyl, n- and isopropyl, ethyl and methyl. "$C_{1-6}$ alkyl", "$C_{1-4}$ alkyl" and "$C_{1-2}$ alkyl" shall be understood in an analogous manner, as shall "$C_{1-6}$ alkoxy" and "$C_{1-4}$ alkoxy".

The term "$C_{2-8}$ alkenyl" means linear or branched chain alkenyl groups having from 2 to 8 carbon atoms and includes all of the hexenyl and pentenyl isomers as well as 1-butenyl, 2-butenyl, 3-butenyl, isobutenyl, 1-propenyl, 2-propenyl, and ethenyl (or vinyl).

The term "$C_{2-8}$ alkynyl" means linear or branched chain alkynyl groups having from 2 to 8 carbon atoms and includes all of the octynyl, heptynyl, hexynyl and pentynyl isomers as well as 1-butynyl, 2-butynyl, 3-butynyl, 1-propynyl, 2-propynyl, and ethynyl (or acetylenyl).

The term "$C_{3-8}$ cycloalkyl" means a cyclic alkane ring having three to eight total carbon atoms (i.e., cyclopropyl, cyclobutyl, cyclopentyl, cyclohexyl, cycloheptyl, or cyclooctyl). The term "C$_{4-7}$ cycloalkyl" refers to a cyclic ring selected from cyclobutyl, cyclopentyl, cyclohexyl and cycloheptyl.

The term "halogen" refers to fluorine, chlorine, bromine and iodine.

The term "heteroaryl" as used herein is intended to include the following groups: furanyl, imidazolyl, isothiazolyl, isoxazolyl, oxadiazolyl, oxazolyl, pyrazinyl, pyrazolyl, pyridazinyl, pyridazinyl, pyridyl, pyrimidyl, pyrrolyl, tetrazolyl, thiadiazolyl, thiazolyl, thienyl, triazolyl and pyrrolidinyl.

The terms "thiophenyl" and "thienyl" have the same meaning herein and are used interchangeably. Similarly, the following pair of terms has the same meaning: "pyridinyl" and "pyridyl".

Exemplary compounds of the present invention include:
3-(4-(1-methylethyl)piperazin-1-ylmethyl)-2-phenyl-quinoline-4-carboxylic acid azepan-1-ylamide; and
3-(4-methylethyl)piperazin-1-ylmethyl)-2-phenyl-quinoline-4-carboxylic acid N'-(1-phenyl-propyl)-hydrazide;
methyl 2-{[3-methyloxy-2-phenyl-4-quinolinyl]carbonyl}-1-phenylhydrazinecarboxylate;
N'-ethyl-3-methyloxy-N',2-diphenyl-4-quinolinecarbohydrazide;
3-methyloxy-2-phenyl-N'-(1-phenylpropyl)-4-quinolinecarbohydrazide;

and their pharmaceutically acceptable salts.

Further compounds of interest include:
3-methyl-N',N',2-triphenyl-4-quinolinecarbohydrazide;
N',3-dimethyl-N',2-diphenyl-4-quinolinecarbohydrazide;
3-methyl-N',2-diphenyl-N'-phenylmethyl-4-quinolinecarbohydrazide;
N-hexahydrocyclopenta[c]pyrrol-2(1H)-yl-3-methyl-2-phenyl-4-quinolinecarboxamide;
N'-cyclopentyl-3-methyl-2-phenyl-N'-propyl-4-quinolinecarbohydrazide;
N'-cyclohexyl-3-{[4-(1-methylethyl)-1-piperazinyl]methyl}-2-phenyl-4-quinolinecarbohydrazide;
N-hexahydro-1H-azepin-1-yl-3-methyl-2-phenyl-4-quinolinecarboxamide;

and their pharmaceutically acceptable salts.

These compounds and those defined by the immediately preceding definitions are especially useful as NK-2 and/or NK-3 antagonists, particularly as NK-3 antagonists.

The terms "administration of" and or "administering a" compound should be understood to mean providing a compound of the invention to the individual in need of treatment.

The term "subject," (alternatively referred to herein as "patient") as used herein refers to an animal, preferably a mammal, most preferably a human, who has been the object of treatment, observation or experiment.

The compounds of the present invention may be administered in the form of pharmaceutically acceptable salts. The term "pharmaceutically acceptable salt" is intended to include all acceptable salts such as acetate, lactobionate, benzenesulfonate, laurate, benzoate, malate, bicarbonate, maleate, bisulfate, mandelate, bitartrate, mesylate, borate, methylbromide, bromide, methylnitrate, calcium edetate, methylsulfate, camsylate, mucate, carbonate, napsylate, chloride, nitrate, clavulanate, N-methylglucamine, citrate, ammonium salt, dihydrochloride, oleate, edetate, oxalate, edisylate, pamoate (embonate), estolate, palmitate, esylate, pantothenate, fumarate, phosphate/diphosphate, gluceptate, polygalacturonate, gluconate, salicylate, glutamate, stearate, glycollylarsanilate, sulfate, hexylresorcinate, subacetate, hydrabamine, succinate, hydrobromide, tannate, hydrochloride, tartrate, hydroxynaphthoate, teoclate, iodide, tosylate, isothionate, triethiodide, lactate, panoate, valerate, and the like which can be used as a dosage form for modifying the solubility or hydrolysis characteristics or can be used in sustained release or pro-drug formulations. Depending on the particular functionality of the compound of the present invention, pharmaceutically acceptable salts of the compounds of this invention include those formed from cations such as sodium, potassium, aluminum, calcium, lithium, magnesium, zinc, and from bases such as ammonia, ethylenediamine, N-methyl-glutamine, lysine, arginine, ornithine, choline, N,N'-dibenzylethylene-diamine, chloroprocaine, diethanolamine, procaine, N-benzylphenethyl-amine, diethylamine, piperazine, tris(hydroxymethyl)aminomethane, and tetramethylammonium hydroxide. These salts may be prepared by standard procedures, e.g. by reacting a free acid with a suitable organic or inorganic base. Where a basic group is present, such as amino, an acidic salt, i.e. hydrochloride, hydrobromide, acetate, pamoate, and the like, can be used as the dosage form.

Also, in the case of an alcohol group being present, pharmaceutically acceptable esters can be employed, e.g. acetate, maleate, pivaloyloxymethyl, and the like, and those esters known in the art for modifying solubility or hydrolysis characteristics for use as sustained release or prodrug formulations.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the present invention are employed. (For purposes of this application, topical application shall include mouthwashes and gargles.)

The pharmaceutical composition and method of the present invention may further comprise other therapeutically active compounds as noted herein which are usually applied in the treatment of the above mentioned pathological conditions.

In the treatment or prevention of conditions which require chemokine receptor modulation an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, preferably once or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

The present invention also provides pharmaceutical compositions comprising a compound of formula I or a pharmaceutically acceptable salt thereof and a pharmaceutically acceptable excipient.

Thus there is provided a compound of formula I or a pharmaceutically acceptable salt thereof for use in a method of treatment of the human or animal body by therapy.

Likewise there is provided the use of a compound of formula I for the manufacture of a medicament for treating a neurokinin-2 and/or neurokinin-3 mediated disease such as schizophrenia, COPD, asthma or irritable bowel syndrome.

There is also disclosed a method of treatment of a subject suffering from a neurokinin-2 and/or neurokinin-3 mediated disease, such as schizophrenia, COPD, asthma or irritable bowel syndrome, which comprises administering to that patient a therapeutically effective amount of a compound of formula I or a pharmaceutically acceptable salt thereof.

The compounds for use in the present invention are generally active in the following tests. They normally have an $IC_{50}$ of less than 1 μM and preferably less than 100 nM.

Details of the NK-2 receptor and its heterologous expression can be found in Gerard et al, J. Biol. Chem., 265: 20455-20462, 1990 and Huang et al, Biochem., 33: 3007-3013, 1994. The latter paper also contains details of mutant scanning.

Details of the NK-3 receptor and its heterologous expression can be found in Huang et al, BBRC, 1992, 184: 966-972 and Sadowski et al, Neuropeptides, 1993, 24: 317-319.

A membrane preparation is prepared as follows. A 10-layer cell factory is seeded with CHO cells stably expressing NK-3 receptors. The CHO cells are prepared in a triple T175 flask in II growth medium which contains Iscore's modified Dulbecco's medium containing 10 ml/l 200 mM L-Glutatine, 10 ml/l penicillin-streptomycin, one vial of hypoxanthine-thymidine 500×/l, 1 mg/ml geneticin and 10% fetal bovine serum (inactivated). The cells are grown for 3 days in an incubator. The medium is washed off and the factory is rinsed twice with 400 ml PBS (Ca, Mg-free). 400 ml enzyme free dissoc. solution (EFDS) is added and the factory is maintained for 10 min at room temperature. The cells are dislodged and the suspension poured into 500 ml centrifuge bottles. The process is repeated with 200 ml EFDS and the mixtures pooled giving 6 bottles in all, which are spun in a centrifuge for 10 min at 2200 rpm.

The supernatants are aspirated and the residual cell pellets are frozen at −80° for 30 min to improve cell lysis and then resuspended in 40 ml Tris with inhibitors per cell factory. The cells are homogenized in 40 ml aliquots with 8 strokes of a glass-teflon grinder at setting 40. The homogenate is transferred to 50 ml centrifuge tubes and placed on a rocker for 15 min at r.t. The homogenate is rehomogenised and held on ice if necessary before being centrifuged again as above.

The supernatant is transferred to Sorvall tubes for an SS-34 roter and held on ice.

40 ml cold Tris with inhibitors is used to resuspend and combine the pellets which are again spun as above. The supernatants are again transferred to Sorvall tubes which, with those above, are spun at 18000 rpm for 20 min.

The supernatants are discarded and the pellets resuspended in a Storage Buffer consisting of 2.50 ml 1M Tris pH7.4, 50 μl 1000× protease inhibitors (4 mg/ml leupeptin (Sigmo), 40 mg/ml Bacitracin (Sigma) and 10 mM phosphoranidon (Peninsula) all dissolved in water) plus 0.5 ml 0.5M $MnCl_2$ made up to 50 ml with $H_2O_{dd}$. A 10 ml syringe is used with 20-, 23- and 25-gauge needles sequentially.

A Bradford protein assay in conducted on 2-10 μl aliquots with BSA as standard before 500-1000 μl aliquots are snap-frozen in liquid nitrogen for storage at −80° C.

The membrane binding assay is carried out as follows. The amount of membranes needed to specifically bind ≦10% of $^{125}$I-NeurokinB is predetermined. The frozen stocks are then diluted to allow addition in 50 μl.

The test compounds are dissolved in DMSO. An automated apparatus (Tecan) is programmed to add 5 μl of compound or DMSO, approximately 100,000 cpm of isotope in 20 μl buffer which is prepared from 50 μMTris, pH7.5, 150 μM NaCl, bovine serum albumin to 0.02%, and protease inhibitors as in the storage buffer, made up as 0.5M stock, and 175 μl assay buffer (as the storage buffer but containing 5 μM $MnCl_2$ and without NaCl) into deep well Marsh boxes (Marsh Biomedical Products) in a 96-well format. Excess unlabelled competing peptide is added by hand for non-specific binding as indicated below. The binding reaction is initiated by adding 50 μl of cell membranes. The tubes are incubated with shaking for 1 h at r.t. and filtered on a Tomtec 96 well cell harvester using Mach III filtermats (Tomtec) or using either a Packard 96-well harvester or Tomtec 9600 using Unifilter GF/C (Packard), presoaked in 0.25% polyethyleneimine and washed five times with 1× wash buffer (0.1M.Tris, pH7.4 and 1M NaCl, 1×=100 ml of 10× stock per liter of cold distilled water). If using Unifilter plates, 60 μl Microscint 20 (Packard) is added to each well and the plate is then heat-sealed before counting in a Packard Topcount. Alternatively the filters from the filtermat are placed in 75×100 mm plastic tubes and counted on a Cobra gamma counter.

For the assay, typically 10 μg of membrane is used at 25,000 cpm which is filtered over a Unifilter GF/C presoaked in 0.5% BSA.

Assays for binding at the neurokinin-2 receptor can be carried out in an analogous manner.

Abbreviations used in the instant specification, particularly the Schemes and Examples, include the following:

Ac=acetyl
9-BBN=9-borabicyclo[3.3.1]nonane
Bn=benzyl
BOC or Boc=t-butyloxycarbonyl
Bu=butyl
t-Bu=tert-butyl
CBZ=carbobenzoxy (alternatively, benzyloxycarbonyl)
CDI=carbonyl diimidazole
DAST=(diethylamino)sulfur trifluoride
DCC=dicyclohexyl carbodiimide
DCM=dichloromethane
DIBAL=diisobutylaluminum hydride
DIEA or DIPEA=diisopropylethylamine
DIAD=diisopropylazodicarboxylate
DMF=N,N-dimethylformamide
DMSO=dimethylsulfoxide
EDAC=1-(3-dimethylamino)propyl-3-ethylcarbodiimide
Et=ethyl
ether=diethyl ether
h=hour(s)
HMDS=hexamethyldisilazyl
HOBT or HOBt=1-hydroxy benzotriazole hydrate
KHMDS=potassium hexamethyldisilazide
LDA=lithium diisopropylamide
Me=methyl
m=minute(s)
Ph=phenyl
Pr=propyl
i-Pr=isopropyl
PMB=p-methoxybenzyl
sat'd=saturated aqueous
rt=room temperature
TBSO=t-butyldimethylsiloxy TEA=triethylamine
Tf=triflic or triflate
TFA=trifluoroacetic acid
THF=tetrahydrofuran
TPAP=tetrapropylammonium perruthenate Compounds of formula I can be made by reacting a compound of formula II with a compound of formula III:

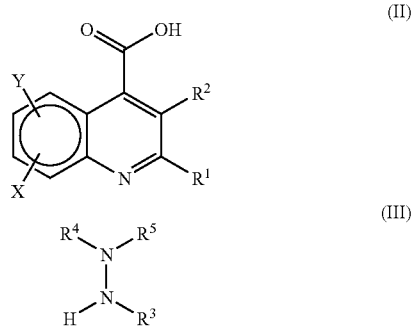

wherein $R^1$, $R^2$, $R^3$, $R^4$, $R^5$, X and Y are as defined above. The reaction is generally carried out in a solvent such as $CH_2Cl_2$ and/or THF in the presence of a base such as $Et_3N$ and a condensing agent such as HBTU or HOBT with EDC.HCl. Depending on the precise nature of the reagents, reaction conditions can range from 1 to 18 hours and from 0° C. to reflux.

If necessary the compound of formula II can be converted into its acid chloride prior to reacting with the compound of formula III; this can be done by reacting with oxalyl chloride for about 18 hours at room temperature.

If desired compounds of formula I can be converted into other compounds of formula I, particularly when it is desired to transform one group $R^5$ into another, by means known in the art. For example, compounds in which $R^5$ is H can be converted into compounds where $R^5$ is methoxycarbonyl by reacting with methyl chloroformate generally in the presence of a base such as $Et_3N$ and a solvent such as $CH_2Cl_2$ for about 4 hours at room temperature.

Compounds of formulae II and III are generally known in the art or can be produced from known compounds by methods known in the art. For example, compounds of formula II can be made by reacting compounds of formulae IV and IV:

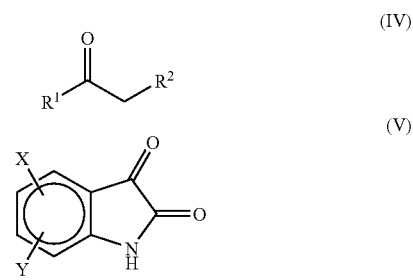

wherein $R^1$, $R^2$, X and Y are as defined above. The reaction is generally carried out in the presence of a strong base such as potassium hydroxide, a solvent such as ethanol and at reflux.

Compounds of formulae IV and V are known in the art or can be made by known methods from known compounds.

Compounds of formula II in which $R^2$ is $C_{1-6}$ alkylNR'R" can be made by reacting compounds of formula II in which $R^2$ is $C_{1-6}$ alkyl successively with N-bromosuccinimide (generally in a solvent such as $CH_3CN$, at reflux and with an initiation agent such as dibenzoylperoxide) and then HNR'R" (generally in the presence of a base such as diisopropylethylamine, in a solvent such as THF at about 50° C.). During this procedure the carboxyl group of the compound of formula II may be protected as the methyl ester.

Components of formula HNR'R" are known in the art or can be made by known methods from known compounds.

The compounds of the present invention can be readily prepared according to the following reaction schemes and examples, or modifications thereof. Starting materials can be made from procedures known in the art or as illustrated. In these reactions, it is also possible to make use of variants which are themselves known to those of ordinary skill in this art, but are not mentioned in greater detail. Furthermore, other methods for preparing compounds of the invention will be readily apparent to the person of ordinary skill in the art in light of the following reaction schemes and examples. Unless otherwise indicated, the variables are as defined above.

The following Examples illustrate the present invention:

EXAMPLE 1

3-(4-(1-Methylethyl)-piperazin-1-ylmethyl)-2-phenylquinoline-4-carboxylic acid azepan-1-ylamide O-Benzotriazole-N,N,N',N'-tetramethyluronium hexafluorophosphate (HBTU) (156 mg, 0.41 mmol) was added to a stirred mixture of 3-(4-(1-methylethyl)-piperazin-1-ylmethyl)-2-phenyl-quinoline-4-carboxylic acid (100 mg, 0.26 mmol) [J. Med. Chem. 2001, 44, 1675-1689], 1-aminohomopiperidine (47 µL, 0.41 mmol) and $Et_3N$ (178 µL, 1.3 mmol) in THF (5 mL) and $CH_2Cl_2$ (1.5 mL), and the mixture was heated at reflux for 18 h under $N_2$. The solvent was evaporated under reduced pressure, and the residue was dissolved in $CH_2Cl_2$ and washed with $H_2O$, 0.5 N NaOH solution, and $H_2O$. The organic phase was dried ($MgSO_4$) and concentrated under reduced pressure. The residue was purified by reverse phase preparative HPLC affording, after basic work up, the desired hydrazide (28 mg, 17%). $^1$H NMR ($CD_3OD$, 360 MHz), Major rotamer δ 8.05 (1H, d, J=8.3 Hz), 7.96 (1H, d, J=8.3 Hz), 7.83-7.75 (1H, m), 7.72-7.60 (1H, m), 7.55-7.43 (5H, m), 3.66 (2H, s), 3.24-3.17 (4H, m), 2.53 (1H, septet, J=6.5 Hz), 2.45-2.10 (8H, m), 1.86-1.72 (8H, m), 1.00 (6H, d, J=6.5 Hz). MS ($ES^+$) $C_{30}H_{39}N_5O$ requires: 485, found: 486 ($M+H^+$, 100%).

EXAMPLE 2

3-(4-(1-Methylethyl)-piperazin-1-ylmethyl)-2-phenylquinoline-4-carboxylic acid N'-(1-phenylpropyl) hydrazide The reaction was carried out according to the procedure described in Example 1 using 3-(4-(1-methylethyl)-piperazin-1-ylmethyl)-2-phenyiquinoline-4-carboxylic acid (100 mg, 0.26 mmol), (1-phenylpropyl)hydrazine.2HCl (152 mg, 0.822 mmol), HBTU (312 mg, 0.822 mmol) and $Et_3N$ (356 µL, 2.57 mmol) to yield the desired hydrazide (35 mg, 26%). $^1$H NMR ($CD_3OD$, 360 MHz) δ 7.97 (1H, d, J=8.3 Hz), 7.70 (1H, t, J=8.3 Hz), 7.55-7.30 (12H, m), 5.48 (1H, s), 4.15 (1H, broad s), 3.60-3.40 (4H, m), 2.81 (2H, s), 2.53 (1H, septet, J=6.4 Hz), 2.40-1.70 (7H, m), 1.01 (6H, d, J=6.4 Hz), 0.90 (3H, t, J=7.5 Hz). MS ($ES^+$) $C_{33}H_{39}N_5O$ requires: 521, found: 522 ($M+H^+$, 100%).

EXAMPLE 3

Methyl 2-{[3-methyloxy-2-phenyl-4-quinolinyl]carbonyl}-1-phenylhydrazinecarboxylate Step 1: 3-Methyloxy-N',2-diphenyl-4-quinolinecarbohydrazide 1-[3-(Dimethylamino)propyl]-3-ethylcarbodiimide hydrochloride (518 mg, 2.7 mmol) was added portionwise to a mixture of 1-hydroxybenzotriazole (365 mg, 2.7 mmol), 3-methyloxy-2-phenylquinoline-4-carboxylic acid (500 mg, 1.8 mmol) [*J. Med. Chem.* 1999, 42, 1053-1065], phenylhydrazine (228 µL, 2.3 mmol) and Et$_3$N (373 µL, 2.7 mmol) in THF (40 mL) at 0° C. After stirring at 0° C. for 1 h the cooling bath was removed and the mixture stirred at room temperature for 3 h. The solvent was evaporated under reduced pressure, and the residue was dissolved in ethyl acetate (50 mL) and washed with H$_2$O (2×50 mL), NaHCO$_3$ (sat., 50 mL), 1N citric acid (50 mL) and brine (50 mL). The organic phase was dried (MgSO$_4$) and concentrated under reduced pressure. The residue was purified by column chromatography on silica gel, eluting with isohexane:ethyl acetate (1:1), to afford the hydrazide (400 mg, 61%) as a yellow solid. $^1$H NMR (CDCl$_3$, 400 MHz), δ 8.16 (1H, d, J=7.4 Hz), 8.06-8.02 (2H, m), 7.95-7.92 (2H, m), 7.70 (1H, dt, J=7.0 and 1.4 Hz), 7.60-7.48 (4H, m), 7.32 (2H, dt, J=7.4 and 1.0 Hz), 7.10-7.07 (2H, m), 6.99 (1H, t, J=7.4 Hz), 6.50 (1H, d, J=4.2 Hz), 3.62 (3H, s). MS (ES$^+$) C$_{23}$H$_{19}$N$_3$O$_2$ requires: 369, found: 370 (M+H$^+$, 100%).

Step 2: Methyl 2-{[3-methyloxy-2-phenyl-4-quinolinyl]carbonyl}-1-phenylhydrazinecarboxylate To a solution of 3-methyloxy-N',2-diphenyl-4-quinolinecarbohydrazide (100 mg, 0.27 mmol) and Et$_3$N (56 µL, 0.41 mmol) in CH$_2$Cl$_2$ (7 mL) was added methyl chloroformate (27 µL, 0.35 mmol). After stirring at room temperature for 4 h the mixture was diluted with CH$_2$Cl$_2$ and washed with 1N HCl (20 mL), 1N NaOH (20 mL) and brine (20 mL). The organic phase was dried (MgSO$_4$) and concentrated under reduced pressure. The residue was purified by column chromatography on silica gel, eluting with isohexane:ethyl acetate (2:1), to afford the title compound (59 mg, 51%) as a colourless foam. $^1$H NMR (CDCl$_3$, 360 MHz), δ 8.43 (1H, s), 8.16-8.13 (2H, m), 8.02-8.00 (2H, m), 7.69 (1H, dt, J=6.9 and 1.3 Hz), 7.61-7.41 (8H, m), 7.30 (1H, t, J=7.4 Hz), 3.91 (3H, s), 3.57 (3H, s). MS (ES$^+$) C$_{25}$H$_{21}$N$_3$O$_4$ requires: 427, found: 428 (M+H$^+$, 100%).

EXAMPLE 4

N'-Ethyl-3-methyloxy-N',2-diphenyl-4-quinolinecarbohydrazide

Step 1: 3-Methyloxy-2-phenyl-4-quinolinecarbonyl chloride

3-Methyloxy-2-phenylquinoline-4-carboxylic acid (200 mg, 0.72 mmol) [*J. Med. Chem.* 1999, 42, 1053-1065] was suspended in CH$_2$Cl$_2$ (5 mL) at 0° C. and oxalyl chloride (62 µL, 0.72 mmol) was added with stirring. After stirring at 0° C. for 1 h the cooling bath was removed and the solution allowed to stir at room temperature for 18 h. After this time the solvent was evaporated and the crude acid chloride used in the subsequent reaction without further purification.

Step 2: N'-Ethyl-3-methyloxy-N',2-diphenyl-4-quinolinecarbohydrazide

The 3-methyloxy-2-phenyl-4-quinolinecarbonyl chloride obtained in Step 1 was dissolved in CH$_2$Cl$_2$ (2 mL) and added dropwise to a solution of Et$_3$N (104 µL, 0.76 mmol) and 1-ethyl-1-phenylhydrazine (102 mg, 0.76 mmol) [*Synthesis* 1983, 157-158] in CH$_2$Cl$_2$ (3 mL) at 0° C. After stirring at 0° C. for 2 h the cooling bath was removed and the solution stirred at room temperature for 18 h. The solvent was evaporated and the residue taken up in ethyl acetate (20 mL). The organic phase was washed with H$_2$O (2×10 mL), 1N NaOH (20 mL) and brine (20 mL). The organic phase was separated, dried (MgSO$_4$) and concentrated under reduced pressure. The residue was purified by column chromatography on silica gel, eluting with isohexane:ethyl acetate (2:1). The fractions containing the desired product were combined, evaporated and triturated with diethyl ether. The title compound (159 mg, 53%) was isolated as a colourless solid. $^1$H NMR (CDCl$_3$, 400 MHz), δ 8.09 (1H, d, J=7.6 Hz), 7.96-7.93 (2H, m), 7.70 (1H, d, J=7.6 Hz), 7.63 (1H, dt, J=7.0 and 1.4 Hz), 7.51-7.45 (6H, m), 7.42-7.28 (4H, m), 5.36-5.35 (1H, broad s), 4.21-4.19 (1H, m), 3.48 (3H, s). MS (ES$^+$) C$_{26}$H$_{25}$N$_3$O$_2$ requires: 411, found: 412 (M+H$^+$, 100%).

EXAMPLE 5

3-Methyloxy-2-phenyl-N'-(1-phenylpropyl)-4-quinolinecarbohydrazide

The reaction was carried out according to the procedure described in Example 3, Step 1 using 3-methyloxy-2-phenylquinoline-4-carboxylic acid (100 mg, 0.36 mmol) [*J. Med. Chem.* 1999, 42, 1053-1065], (1-phenylpropyl)hydrazine.2HCl (104 mg, 0.47 mmol), 1-hydroxybenzotriazole (73 mg, 0.54 mmol) and Et$_3$N (204 µL, 1.48 mmol) in THF (8 mL). The residue was purified by column chromatography on silica gel, eluting with isohexane:ethyl acetate (2:1), to afford the hydrazide (106 mg, 72%) as a colourless foam. $^1$H NMR (CDCl$_3$, 400 MHz), δ 8.18 (1H, d, J=8.9 Hz), 8.06-8.04 (2H, m), 8.01 (1H, dd, J=8.9 and 0.9 Hz), 7.71 (1H, dt, J=7.0 and 1.4 Hz), 7.64-7.59 (2H, m), 7.56-7.50 (3H, m), 7.33 (2H, dt, J=7.3 and 1.9 Hz), 7.13 (2H, d, J=7.9 Hz), 6.94 (1H, t, J=7.2 Hz), 3.80 (2H, q, J=7.2 Hz), 3.66 (3H, s), 1.21 (3H, t, J=7.2 Hz). MS (ES$^+$) C$_{25}$H$_{23}$N$_3$O$_2$ requires: 397, found: 398 (M+H$^+$, 100%).

The invention claimed is:
1. A compound of Formula (I):

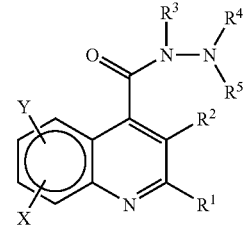

wherein:
R$^1$ is an aryl or heteroaryl ring, wherein aryl is phenyl or naphthyl and heteroaryl is a 5-membered unsaturated ring containing 1, 2, 3 or 4 nitrogen atoms and/or, an oxygen or sulphur atom provided no more than two nitrogen atoms are present, or a 6-membered unsaturated ring containing 1, 2 or 3 nitrogen atoms, said ring being optionally substituted by one, two or three groups independently chosen from hydroxy, halogen, nitro, cyano, amino, CF$_3$, C$_{1-4}$ alkyl, C$_{2-4}$ alkenyl and C$_{2-4}$ alkynyl;

R² is selected from the group consisting of: $C_{1-6}$ alkoxy, $C_{1-6}$ alkyl, $C_{1-4}$ alkyl substituted by NR'R", and $C_{1-6}$ alkoxy substituted by NR'R", where R' and R" are independently selected from hydrogen and $C_{1-4}$ alkyl, or where R' and R", together with the nitrogen atom to which they are attached, form a saturated nitrogen-containing 3-7 membered heterocycle optionally containing a further nitrogen atom and optionally substituted by NR'R" as defined above;

R³ is hydrogen or $C_{1-6}$ alkyl;

R⁴ is selected from: hydrogen, $C_{1-8}$ alkyl, $C_{2-8}$ alkenyl, $C_{2-8}$ alkynyl, $C_{3-8}$ cycloalkyl, aryl and aryl $C_{1-6}$ alkyl;

R⁵ is hydrogen, $C_{1-8}$ alkyl, $C_{2-8}$ alkenyl, $C_{2-8}$ alkynyl, $C_{3-8}$ cycloalkyl, aryl, aryl $C_{1-6}$ alkyl or $C_{1-6}$ alkoxycarbonyl;

or R⁴ and R⁵, together with the nitrogen atom to which they are attached, form a $C_3$-$C_{10}$ mono- or bicyclic saturated ring;

X and Y are independently selected from: hydrogen, hydroxy, nitro, amino, cyano, $CF_3$, halogen and $C_{1-4}$ alkyl;

or a pharmaceutically acceptable salt thereof.

2. The compound of claim 1 wherein R¹ is unsubstituted or monosubstituted by hydroxy, halogen, nitro, cyano, amino, $CF_3$ or $CH_3$.

3. The compound of claim 2 wherein R¹ is phenyl.

4. The compound of claim 1 wherein R' and R" are independently selected from: hydrogen, methyl, ethyl and propyl, or R' and R", together with the nitrogen atom to which they are attached, form a piperidine or piperazine ring optionally substituted by $C_{1-4}$ alkyl.

5. The compound of claim 1 wherein R⁴ is selected from: $C_{1-8}$ alkyl, $C_{3-8}$ cycloalkyl, aryl, and aryl $C_{1-6}$ alkyl.

6. The compound of claim 1 wherein R⁵ is selected from: hydrogen, $C_{1-6}$ alkyl, aryl, and $C_{1-4}$ alkoxycarbonyl.

7. The compound of claim 1 wherein X and Y are independently hydrogen or methyl.

8. A compound which is selected from the group consisting of:

3-(4-(1-methylethyl)piperazin-1-ylmethyl)-2-phenyl-quinoline-4-carboxylic acid azepan-1-ylamide;

3-(4-methylethyl)piperazin-1-ylmethyl)-2-phenyl-quinoline-4-carboxylic acid N'-(1-phenyl-propyl)-hydrazide;

methyl2-{[3-methyloxy-2-phenyl-4-quinolinyl]carbonyl}-1-phenylhydrazinecarboxylate;

N'-ethyl-3-methyloxy-N',2-diphenyl-4-quinolinecarbohydrazide; and 3-methyloxy-2-phenyl-N'-(1-phenylpropyl)-4-quinolinecarbohydrazide;

or a pharmaceutically acceptable salt thereof.

9. A compound which is selected from the group consisting of:

3-methyl-N',N',2-triphenyl-4-quinolinecarbohydrazide;

N',3-dimethyl-N',2-diphenyl-4-quinolinecarbohydrazide;

3-methyl-N',2-diphenyl-N'-phenylmethyl-4-quinolinecarbohydrazide;

N-hexahydrocyclopenta[c]pyrrol-2(1H)-yl-3-methyl-2-phenyl-4-quinolinecarboxamide;

N'-cyclopentyl-3-methyl-2-phenyl-N'-propyl-4-quinolinecarbohydrazide;

N'-cyclohexyl-3-{[4-(1-methylethyl)-1-piperazinyl]methyl}-2-phenyl-4-quinolinecarbohydrazide; and N-hexahydro-1H-azepin-1-yl-3-methyl-2-phenyl-4-quinolinecarboxamide;

or a pharmaceutically acceptable salt thereof.

10. A pharmaceutical composition comprising a pharmaceutically acceptable excipient and the compound of claim 1 or a pharmaceutically salt thereof.

11. A pharmaceutical composition comprising a pharmaceutically acceptable excipient and the compound of claim 8 or a pharmaceutically salt thereof.

12. A pharmaceutical composition comprising a pharmaceutically acceptable excipient and the compound of claim 9 or a pharmaceutically salt thereof.

* * * * *

UNITED STATES PATENT AND TRADEMARK OFFICE
CERTIFICATE OF CORRECTION

PATENT NO. : 7,482,457 B2  Page 1 of 1
APPLICATION NO. : 10/544440
DATED : January 27, 2009
INVENTOR(S) : Mark Stuart Chambers et al.

It is certified that error appears in the above-identified patent and that said Letters Patent is hereby corrected as shown below:

Title Page, (*) Notice: Subject to any disclaimer, the term of this patent is extended or adjusted under 35 U.S.C. 154(b) by 609 days.

should read (*) Notice: Subject to any disclaimer, the term of this patent is extended or adjusted under 35 U.S.C. 154(b) by 785 days.

Signed and Sealed this

Thirteenth Day of April, 2010

David J. Kappos
*Director of the United States Patent and Trademark Office*